(12) United States Patent
Ono et al.

(10) Patent No.: US 7,722,899 B2
(45) Date of Patent: May 25, 2010

(54) SURFACE-TREATED POWDER AND COSMETIC PREPARATION

(75) Inventors: Ichiro Ono, Gunma (JP); Masanao Kamei, Gunma (JP); Kiyomi Tachibana, Tokyo (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 1681 days.

(21) Appl. No.: 10/479,993

(22) PCT Filed: Jun. 3, 2002

(86) PCT No.: PCT/JP02/05460

§ 371 (c)(1),
(2), (4) Date: Dec. 8, 2003

(87) PCT Pub. No.: WO02/100356

PCT Pub. Date: Dec. 19, 2002

(65) Prior Publication Data

US 2004/0156809 A1    Aug. 12, 2004

(30) Foreign Application Priority Data

Jun. 7, 2001    (JP)    ............... 2001-172334

(51) Int. Cl.
- A61K 9/14    (2006.01)
- A61K 8/02    (2006.01)
- A61Q 5/00    (2006.01)
- A61Q 19/00    (2006.01)
- A61Q 15/00    (2006.01)

(52) U.S. Cl. .............. 424/490; 424/65; 424/70.12; 424/78.02; 424/401; 424/489; 514/844

(58) Field of Classification Search .............. None
See application file for complete search history.

(56) References Cited

U.S. PATENT DOCUMENTS 5,219,560 A    6/1993    Suzuki
5,234,682 A *  8/1993    Macchio et al. .......... 424/69
5,609,852 A *  3/1997    Galley et al. ............ 424/59
5,863,522 A *  1/1999    Forestier et al. ......... 424/59
5,914,101 A *  6/1999    Tapley et al. ............ 424/59
6,235,292 B1*  5/2001    Bara et al. ............. 424/401
2006/0198804 A1*  9/2006    Ono et al. ............. 424/70.7

FOREIGN PATENT DOCUMENTS

| EP | 0 918 069 | 5/1999 |
| EP | 1 065 234 | 1/2001 |
| JP | 63-113081 | 5/1988 |
| JP | 5-339125 | 12/1993 |
| JP | 08 127514 | 5/1996 |
| JP | 9-157543 | 6/1997 |
| JP | 2000204290 | * 7/2000 |

OTHER PUBLICATIONS

STN Accession No. 2000:503508 Abstracting: Masuda JP200204290, Jul. 25, 2000. 12 pages.*
Abstract of JP 08 127514 (Kanebo Ltd) May 21, 1996.

* cited by examiner

*Primary Examiner*—Ernst V Arnold
(74) *Attorney, Agent, or Firm*—Millen, White, Zelano & Branigan, P.C.

(57) ABSTRACT

A surface-treated powder powder which is surface-treated with an acrylic/silicone copolymer having at least one hydrolyzable silyl group in the molecule, and a cosmetic material containing this powder.

The surface-treated powder of this invention preferably contains 0.1-30 wt parts of the acrylic/silicone copolymer relative to 100 wt parts of the powder prior to surface treatment. The acrylic/silicone copolymer preferably comprises a trunk polymer comprising an acrylic polymer, and a branched polymer comprising an organic polysiloxane.

The surface activity of the surface-treated powder of this invention is very well blocked, and it has excellent water resistance and sebum resistance. In addition, the cosmetic material of this invention containing this surface-treated powder has good cosmetic lasting properties, and is highly stable over time.

36 Claims, No Drawings

SURFACE-TREATED POWDER AND COSMETIC PREPARATION

FIELD OF THE INVENTION

This invention relates to a novel surface-treated powder and cosmetic material containing same, and in particular, to a powder whereof the surface activity is blocked by surface treatment, and a long-lasting cosmetic material containing this powder which has a smooth feel when used, dispersibility, water resistance, sebum resistance and stability with time.

BACKGROUND OF THE INVENTION

In general, human secretions such as sweat, tears and sebum spoil cosmetic materials. In particular, with suncut creams and makeup cosmetic materials, sebum secreted by the skin becomes mixed with cosmetic material blending oils, leading to excessive wetting of the cosmetic material which is a major factor causing it to deteriorate. To reduce the oils in the cosmetic material remaining on the skin, it has been attempted to use volatile oil agents such as octamethylcyclotetrasiloxane and decamethylcyclopentasiloxane as a part of the oils which were blended.

Rubbing and water are external factors which spoil makeup. To improve poor makeup lasting properties which occur due to water-soluble substances, such as sweat and tears, to prevent loss of aqueous components or sebum in the skin and to maintain skin protection, silicone oils are blended to improve water repellence. For example, due to their light feel, outstanding water-repellence and high safety, silicone oils such as dimethylpolysiloxane have been used abundantly as oils in cosmetic materials in recent years. At the same time, powders, e.g., pigments such as titanium oxide, zinc oxide, red ocher, mica and sericite are widely used in basic cosmetics, suncut materials, nail colors and nail coats, foundation, mascara and eyeliner. To block the surface activity of these powders and impart water resistance and sebum resistance, it is common to give them a surface treatment such as alumina treatment, silica treatment, oil treatment, metallic soap treatment or organopolysiloxane treatment.

In recent years, in many cases, the organopolysiloxane has a reactive part within the molecule. The organopolysiloxane forms a chemical bond with the powder, which modifies the powder surface and blocks its surface activity. Also, the treatment agent does not secede from the powder surface even if a solvent system cosmetic material is used, and as change of cosmetic material properties due to treatment can be reduced, this is highly effective.

For example, in Japanese Patent (JP-B) No. 2719303, a method of carrying out the surface treatment by 12-60 wt parts of methylhydrogen polysiloxane to 100 wt parts of powder, is disclosed. In Japanese Unexamined Patent Publication (JP-A) No. 07-196946, a surface treatment method which uses a straight chain single terminal alkoxy-modified silicone is disclosed. Thus, powder treatment by a reactive organopolysiloxane is a generally known technique, however in all cases, the blocking of the powder surface activity was insufficient, and in particular, when the treatment agent was a methylhydrogenpolysiloxane (methyl hydrogen polysiloxane or dimethylhydrogenpolysiloxane), as unreacted Si—H groups remained in the powder even after surface treatment when the powder was blended with the cosmetic material, there was a problem of hydrogen gas being generated depending on the condition of liquid properties of the cosmetic material. Moreover, when a powder treated with a single terminal alkoxy-modified silicone was used as a pressed powder cosmetic material, there were few problems regarding water resistance and sebum resistance, but when it was used in a solution system, the treatment effect could not be said to be adequate. This is considered to be due to few reactive sites which react with the powder as compared with a methylhydrogen polysiloxane treatment agent, so that untreated parts remain in the powder surface.

Thus, although conventional powders treated by reactive organopolysiloxane treatment agents had outstanding aspects, they were not effective in all forms of cosmetic materials. A surface-treated powder with improved blocking of surface activity, water resistance and sebum resistance was therefore desired.

As a result of intensive studies carried out to discover a surface-treated powder with improved blocking of surface activity, water resistance and sebum resistance, the Inventors found that by surface-treating the powder with an acrylic/silicone copolymer having at least one hydrolyzable silyl group in the molecule, a good surface-treated powder can be obtained, and by blending this surface-treated powder with a cosmetic material, a cosmetic material which was very pleasant to use, long-lasting and very stable over time was obtained, and thereby arrived at the present invention.

It is therefore a first object of the invention to provide a surface-treated powder having an improved surface treatment (blocking of surface activity, water resistance and sebum resistance).

It is a second object of the invention to provide a cosmetic material which is very pleasant to use, long-lasting and very stable over time.

SUMMARY OF THE INVENTION

The aforesaid objects of the invention were attained by a surface-treated powder which is surface-treated by an acrylic/silicone copolymer having at least one hydrolyzable silyl group in the molecule, and by a cosmetic material containing this powder.

The surface-treated powder of the present invention is a powder which is surface-treated by an acrylic/silicone copolymer having at least one hydrolyzable silyl group in the molecule, the proportion of this acrylic/silicone copolymer preferably being 0.1-30 wt parts relative to 100 wt parts of the powder prior to surface treatment.

The aforesaid acrylic/silicone copolymer preferably comprises a trunk polymer comprising an acrylic polymer, and a branch polymer comprising an organopolysiloxane.

Further, the acrylic/silicone copolymer is preferably obtained by copolymerization of 1-97 wt % of the organopolysiloxane compound represented by the following general formula (1),

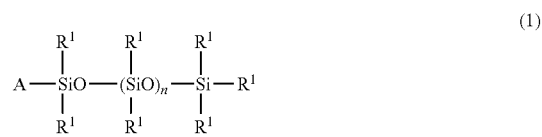

(1)

wherein, A in the formula is the radical polymerizing group represented by:

$$CH_2=C(R^2)COOR^3 \quad (4)$$

$$CH_2=C(R^2)C_6H_5- \quad (5)$$

(in the formulae, $R^2$ is hydrogen or a methyl group, $R^3$ is an alkylene group having 1-10 carbon atoms, and n is 3-500), and $R^1$ are organic groups selected from alkyl groups, aryl, aralkyl and fluorine-substituted alkyl groups having 1-30 carbon atoms, which may be identical or different;

0-95 wt % of the acrylic-monomer represented by the following general formula (2):

$$CH_2=C(R^4)COOR^5 \quad (2)$$

wherein, $R^4$ in the formula is hydrogen or methyl, and $R^5$ is an alkyl group having 1-30 carbon atoms;

and 1-10 wt % of the radical polymerizing silane compound represented by the following general formula (3):

$$B-Si(CH_3)_{3-m}(OR^6)_m \quad (3)$$

wherein, B in the formula is a radical polymerizing group having the following general formula (6) or (7):

$$CH_2=C(R^7)COOR^8- \quad (6)$$

$$CH_2=C(R^7)C_6H_5- \quad (7)$$

wherein, $R^7$ is hydrogen or methyl, $R^8$ is an alkylene group having 1-10 carbon atoms, and $R^6$ is an alkyl or alkenyl group having 1-4 carbon atoms, and m is 1-3.

DESCRIPTION OF THE PREFERRED EMBODIMENTS

The surface-treated powder of the present invention is obtained by treating a powder with an acrylic/silicone copolymer having at least one hydrolyzable silyl group in the molecule. There is no particular limitation on this acrylic/silicone copolymer provided that it has at least one hydrolyzable silyl group in the molecule. It may be a block copolymer or a graft copolymer, but from the viewpoint of adsorption on the powder, reactivity therewith and properties of the surface-treated powder, it is preferably an acrylic/silicone-graft copolymer wherein the trunk polymer is an acrylic polymer and the branch polymer is an organopolysiloxane.

There is no particular limitation on the method of manufacturing this acrylic/silicone graft polymer. The organopolysiloxane may be made to react with the acrylic-polymer manufactured beforehand, but from the viewpoint of ease of manufacture and molecular design, the macromonomer method, wherein an organopolysiloxane compound having the radical polymerizing group represented by the following general formula (1), the acrylic monomer represented by the following general formula (2), and the radical polymerizing silane compound represented by the following general formula (3) are copolymerized together, is convenient.

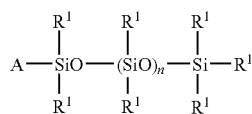

(1)

wherein, A in the formula is a radical polymerizing group represented by the following general formulae (4) or (5):

$$CH_2=C(R^2)COOR^3- \quad (4)$$

$$CH_2=C(R^2)C_6H_5- \quad (5)$$

(wherein, $R^2$ is hydrogen or methyl, $R^3$ is an alkylene group having 1-10 carbon atoms and n is 3-500), and $R^1$ are organic groups selected from alkyl groups, aryl, aralkyl and fluorine-substituted alkyl groups having 1-30 carbon atoms, and may be identical or different.

The organopolysiloxane compound having the radical polymerizing group represented by the aforesaid general formula (1) is known as a silicone macromonomer, and it has a radical polymerizing group at only one terminal. Herein, A may be a monovalent organic group having radical polymerizing properties, and can be specifically represented by the aforesaid general formulae (4) or (5). Examples of A are (meth)acryloxy methyl, (meth)acryloxy propyl, (meth)acryloxy decyl, styryl and alpha-methylstyryl. Examples of $R^1$ are alkyl groups such as methyl, ethyl, propyl, butyl, pentyl, hexyl, heptyl, octyl, nonyl, decyl and cyclohexyl, aryl groups such as phenyl and tolyl, aralkyl groups such as benzyl and phenethyl, and fluorine-substituted alkyl groups such as trifluoropropyl and nonafluorobutylethyl, but from the viewpoint of dispersibility in solvent when the surface-treated powder is blended with the cosmetic material, water resistance of the makeup film, sebum resistance and feel, it is preferably mostly methyl.

n is an integer in the range 3-500, but preferably 9-200. If it is less than 3, the properties of the silicone are poor, so dispersibility in solvent when the surface-treated powder is blended with the cosmetic material, water resistance of the makeup film and sebum resistance are inadequate, whereas if it is more than 500, copolymerizing properties with the acrylic monomer or radical polymerizing silane compound are poorer, and it is difficult to obtain a good copolymer.

The organopolysiloxane compound having the radical polymerizing group shown by the aforesaid formula (1) may be synthesized by the method described in JP-A No. 07-224168, specific examples being as shown below.

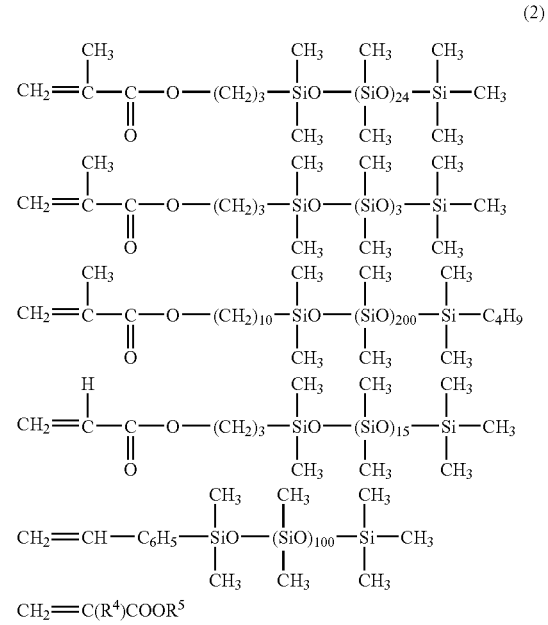

wherein, $R^4$ is hydrogen or methyl, and $R^5$ is an alkyl group having 1-30 carbon atoms.

Specific examples of the acrylic monomer of the aforesaid general formula (2) are methyl (meth)acrylate, ethyl (meth)acrylate, isopropyl (meth)acrylate, n-butyl (meth)acrylate, t-butyl (meth)acrylate and cyclohexyl (meth)acrylate, 2-ethyl hexyl (meth)acrylate, tridecyl (meth)acrylate, stearyl (meth) acrylate, isostearyl (meth)acrylate and behenyl (meth)acrylate. These may be used alone, or two or more may be used together.

$$B-Si(CH_3)_{3-m}(OR^6)_m \quad (3)$$

wherein, B is the radical polymerizing group represented by the following general formulae (6) or (7):

$$CH_2=C(R^7)COOR^8- \quad (6)$$

$$CH_2=C(R^7)C_6H_5- \quad (7)$$

(wherein, $R^7$ is hydrogen or methyl, $R^8$ is an alkylene group having 1-10 carbon atoms, $R^6$ is an alkyl group or alkenyl group having 1-4 carbon atoms, and m is 1-3).

The hydrolyzable silyl group of the present invention is preferably a silyl group represented by the following formula:

$$-Si(CH_3)_{3-m}(OR^6)_m$$

(wherein, $R^6$ and m are identical to the above), and this is introduced into the acrylic/silicone copolymer of the invention by the radical polymerizing silane compound represented by the aforesaid general formula (3).

B in the radical polymerizing silane compound represented by the general formula (3), is an identical group to the aforesaid A. Examples of the radical polymerizing silane compound represented by this general formula (3), are:

γ-methacryloxypropyl trimethoxysilane, γ-methacryloxypropyl methyldimethoxysilane, γ-methacryloxypropyl dimethylmethoxysilane, γ-methacryloxypropyl triethoxysilane, γ-methacryloxypropyl methyldiethoxysilane, γ-methacryloxypropyl tributoxysilane, γ-methacryloxypropyl triisopropenoxysilane; γ-acryloxypropyl trimethoxysilane, acryloxy methyltrimethoxysilane, γ-acryloxypropyl triethoxysilane, γ-acryloxypropyl methyldiethoxysilane, styryl trimethoxysilane, styryl triethoxysilane and α-methyl styryl trimethoxysilane. These may be used alone, or two or more may be used together.

The proportion of compounds represented by the aforesaid general formulae (1), (2) and (3) used for copolymerization, is such that the organopolysiloxane compound having the radical polymerizing group of general formula (1) is 1-97 wt %, but preferably 5-90 wt %, the acrylic monomer of general formula (2) is 0-95 wt %, but preferably 2-60 wt %, and the radical polymerizing silane compound of general formula (3) is 1-10 wt %, but preferably 2-7 wt %.

When there is too little of the organopolysiloxane compound having the radical polymerizing group of general formula (1), dispersibility in oils when blending the surface-treated powder with the cosmetic material, water resistance of makeup film and sebum resistance are not fully acquired, but if it is too large, adsorption and reactivity with powder falls. If there is too much of the acrylic monomer of general formula (2), water resistance of the makeup film and sebum resistance are not fully acquired. Moreover, if there is too little of the radical polymerizing silane compound of general formula (3), reactivity will fall, and if it is too large, reactions occur not only on the powder surface but also within the treatment agent, so the powder easily condenses.

Although this acrylic/silicone-graft copolymer can be obtained by copolymerization of the aforesaid components, it is also possible to use other radical polymerizing compounds within a range which does not impair the features of the invention, if required. Examples of these other radical polymerizing compounds are carboxylic acids such as (meth) acrylic acid, fumaric acid and maleic acid, hydroxyalkyl esters such as (meth)acrylic acid hydroxyethyl and (meth) acrylic acid hydroxypropyl, amides such as (meth)acrylamide, fluorine-substituted alkyl esters such as (meth)acrylic acid perfluorooctyl ethyl and (meth)acrylic acid perfluorobutylethyl, styrene, acrylonitrile, vinyl acetate, vinyl pyrrolidone, polyoxyethylene mono(meth)acrylate, polyoxypropylene mono(meth)acrylate, polyoxyethylene/polyoxypropylene mono(meth)acrylate, polycaprolactone mono(meth)acrylate, tris(trimethylsiloxy) silylpropyl methacrylate and tris(trimethylsiloxy) silylstyrene.

The molecular weight of the acrylic/silicone copolymer used for the surface-treated powder of the invention is not particularly limited provided that it has at least one hydrolyzable silyl group in the molecule, but it may be 5,000-200,000 expressed as weight average molecular weight of polystyrene as measured by GPC. If it is less than 5,000, the powder treatment effect is unsatisfactory, and if it is more than 200,000, it is more difficult to use the surface-treated powder when it is blended with the cosmetic material.

The method of manufacturing the acrylic/silicone-copolymer is not particularly limited and any prior art method may be used such as solution polymerization, emulsion polymerization, suspension polymerization and block polymerization, but from the viewpoint of polymer homogeneity and ease of molecular weight adjustment, solution polymerization is the most preferred. In this case, the solvent used is preferably one in which the aforesaid components and polymer can be uniformly dissolved. Examples of such solvents are toluene, xylene, ethanol, isopropyl alcohol, n-butanol, acetone, methyl ethyl ketone, methyl isobutyl ketone, ethyl acetate, n-butyl acetate, isobutyl acetate, diethyl ether and tetrahydrofuran. As polymerization initiator, the usual radical polymerization initiators may be used, e.g., organic peroxides such as benzoyl peroxide and dicumyl peroxide, and azo compounds such as azobisisobutyronitril. To control the molecular weight of the polymer, mercapto compounds, such as dodecyl mercaptan and mercaptopropyltrimethoxy silane, may be used as a chain transfer agent, and, in the case of a hydrolyzable silyl group-containing compound such as mercaptopropyltrimethoxy silane, there is also the advantage that the hydrolyzable silyl group is introduced at the polymer end. The obtained polymer solution may be used as is or diluted for powder treatment, or the solvent may be removed and the polymer extracted alone, or it may be redissolved in another solvent and then used.

Provided that it is any of the powders commonly used for cosmetic materials, the powder used as the surface-treated powder of the invention may have any form (spherical, acicular, tabular), particle diameter (fume, fine particle, pigment) or particle structure (porous, non-porous). Examples are inorganic powders, organic powders, surfactant metal salt powders, colored pigments, pearl pigments, metal powder pigments and natural pigments.

Example of inorganic powders are titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, magnesium silicate, magnesium aluminum silicate, calcium silicate, barium silicate, strontium silicate, metal tungstates, hydroxyapatite, vermiculite, haidilite, bentonite, montmorillonite, hectorite, zeolite, ceramic powder, dibasic calcium phosphate, alumina, aluminum hydroxide, boron nitride and silica etc.

Examples of organic powders are polyamide powder, polyester powder, polyethylene powder, polypropylene powder, polystyrene powder, polyurethane, benzoguanamine powder, polymethyl benzoguanamine powder, polytetrafluoroethylene powder, polymethylmethacrylate powder, cellulose, silk powder, nylon powder such as nylon 12 and nylon 6, crosslinked silicone fine powder having dimethylsilicone crosslinks, polymethyl silsesquioxane, styrene-acrylic acid copolymer, divinylbenzene-styrene copolymer, vinyl resin, urea resin, phenol resin, fluororesin, silicon resin, acrylate resin, melamine resin, epoxy resin, polycarbonate resin, microcrystalline fiber powder, starch powder and lauroyl lysine.

Examples of surfactant metal salt powders (metallic soaps) are zinc stearate, aluminum stearate, calcium stearate, magnesium stearate, zinc myristate, magnesium myristate, zinc cetyl phosphate, calcium cetyl phosphate and zinc sodium cetyl phosphate. Examples of colored pigments are inorganic red pigments such as iron oxide, iron hydroxide and iron titanate, inorganic brown pigments such as γ-iron oxide, inorganic yellow pigments such as iron oxide yellow and ocher, inorganic black pigments such as iron oxide black and carbon black, inorganic violet pigments such as manganese violet and cobalt violet, inorganic green pigments such as chromium hydroxide, chromium oxide, cobalt oxide and cobalt titanate, inorganic blue pigments such as Prussian blue and ultramarine blue, lakes of tar pigment, lakes of natural dyes and synthetic resin powders which are complexes of these powders.

Examples of pearl pigments are titanium dioxide-coated mica, bismuth oxychloride, titanium dioxide-coated bismuth oxychloride, titanium dioxide-coated talc, scales foil and titanium dioxide-coated colored mica; examples of metal powder pigments are aluminum powder, copper powder and stainless steel powder; examples of tar pigments are Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207; and examples of natural pigments are powders selected from among carminic acid, laccainic acid, carthamin, bradilin and crocin.

Also in these powders, according to the present invention, extenders such as zinc oxide, titanium dioxide or mica, sericite, talc or kaolin, are preferred.

The acrylic/silicone-copolymer used as surface treatment agent for these powders may be used for any of its various applications, but it became clear that it is particularly suitable as a powder surface treatment agent. The surface-treated powder of the invention which has been surface-treated with this acrylic/silicone-copolymer has sufficient surface activity blockage with excellent water resistance and sebum resistance, and does not generate hydrogen after treatment, so it is particularly useful for cosmetic materials. In this case, the blending amounts of acrylic/silicone-copolymer and powder are preferably 0.1-30 wt parts and more preferably 0.5-10 wt parts to 100 wt parts of powder.

The powder which is surface-treated by the acrylic/silicone-copolymer of the invention may be obtained for example by using the acrylic/silicone-copolymer as a treatment agent in a well-known treatment method selected from the following treatment methods.

1. The target powder is surface-treated by dispersing it in a treatment agent comprising water or an organic solvent blended with the treatment agent.

2. The powder and treatment agent are mixed, and surface treatment is effected using a crusher such as a ball mill or jet mill.

3. The treatment agent is blended with a solvent, the powder is dispersed therein and the agent is adsorbed on the surface, then the product is dried and sintered.

The surface-treated powder of the present invention can be used for various kinds of applications, but is particularly useful as a starting material for all cosmetic materials used on the skin and hair, such as skin care products, makeup products, hair products, antiperspirants and ultraviolet blocking products. Although it depends on the type and form of the cosmetic material, according to the invention, the surface-treated powder which has been surface-treated with the aforesaid acrylic/silicone-copolymer can be blended in a proportion of 0.1 to 99% wt parts relative to the whole cosmetic material.

The cosmetic material of the present invention contains the aforesaid A) surface-treated powder as an essential ingredient, and may also further at least one moeity selected from among a group comprising B) oils, C) water, D) compounds having an alcoholic hydroxyl group in the molecular structure, E) water-soluble or water-swelling polymers, F) powders and/or colorants other than the surface-treated powder of this invention, G) surfactants, H) crosslinked organopolysiloxanes, and I) silicone resins.

According to the purpose, one, two or more of the B) oils can be blended with the cosmetic material of the invention. If used for an ordinary cosmetic material, any oil may be used. i.e., a solid, semi-solid or liquid oil.

It is moreover preferred that at least part of the oil B) is a liquid at ordinary temperature and that at least part of the oil B) is a straight chain or cyclic silicone oil represented by $R^9_a SiO_{(4-a)/2}$ (wherein, $R^9$ is an organic group selected from among a hydrogen atom, an alkyl group, an aryl group, an aralkyl group and a fluorine-substituted alkyl group having 1-30 carbon atoms, and $0<=a<=2.5$), and particularly preferred that at least part of the oil B) is an oil comprising a fluorine group or an amino group.

Examples of natural animal and vegetable oils and fats, and semi-synthetic oils and fats, are avocado oil, linseed oil, almond oil, Ibota wax, perilla oil, olive oil, cacao butter, kapok wax, kaya oil, carnauba wax, Glycyrrhiza oil, candellila wax, beef tallow, neat's foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shea butter, Chinese tung oil, cinnamon oil, jojoba wax, shellac wax, turtle oil, soybean oil, tea seed oil, camellia oil, evening primrose oil, corn oil, lard, rape seed oil, Japanese tung oil, rice-bran oil, germ oil, horse fat, persic oil, palm oil, palm kernel oil, castor oil, hydrogenated castor oil, caster oil fatty acid methylester, sunflower oil, grapeseed oil, bayberry wax, jojoba oil, macadamia nut oil, beeswax, mink oil, cottonseed oil, cotton wax, Japanese wax, kernel oil, montan wax, coconut oil, hydrogenated coconut oil, triconut oil fatty acid glyceride, mutton-tallow, peanut oil, lanolin, liquid lanolin, hydrogenated lanolin, lanolin alcohol, hard lanolin, lanolin acetate, lanolin fatty acid isopropyl, hexyl laurate, POE lanolin alcohol ether, POE lanolin alcohol acetate, polyethylene glycol lanolin fatty acid, POE hydrogenated lanolin alcohol ether, and egg yolk oil. POE means polyoxyethylene.

Examples of a hydrocarbon oil which can be mixed therein include ozokerite, squalane, squalene, ceresine, paraffin, paraffin wax, liquid paraffin, pristane, polyisobutylene, microcrystalline wax and Vaseline; and those of a higher fatty acid which can be mixed include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Examples of a higher alcohol which can be mixed therein include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol) and monooleyl glyceryl ether (cerakyl alcohol).

Examples of an ester oil which can be mixed therein include diisobutyl adipate, 2-hexyldecyl adipate, di-2-heptylundecyl adipate, N-alkylglycol monoisostearates, isocetyl isostearate, trimethylolpropane triisostearic acid ester, ethylene glycol di-2-ethylhexanoic acid ester, cetyl 2-ethylhexanoate, trimethylolpropane tri-2-ethylhexanoic acid ester, pentaerythritol tetra-2-ethylhexanoic acid ester, cetyl octanoate, octyldodecyl gum ester, oleyl oleate, octyldodecyl oleate, decyl oleate, neopentyl glycol dicapric acid ester, triethyl citrate, 2-ethylhexyl cinnamate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethylocanoate, ethyl laurate, hexyl laurate, N-lauroyl-L-glutaminic acid 2-octyldodecyl ester and diisostearyl malic acid; and examples of a glyceride oil which can be mixed therein include acetoglyceride, triisooctanoic acid glyceride, triisostearic acid glyceride, triisopalmitic acid glyceride, tri-2-ethylhexanoic acid glyceride, monostearic acid glyceride, di-2-heptylundecanoic acid glyceride, trimyristic acid glyceride and myristic acid isostearic acid diglyceride.

As examples of other silicone oils which can be mixed, mention may be made of organopolysiloxanes having from low to high viscosities, such as dimethylpolysiloxane, methylphenylpolysiloxane, methylhydrogenpolysiloxane and dimethylsiloxane-methylphenylsiloxane copolymer; cyclosiloxanes, such as octamethylcyclotetrasiloxane, decamethylcyclopentasiloxane, dodecamethylcyclohexasiloxane, tetramethyltetrahydrogencyclotetrasiloxane; silicone rubbers, such as gummy dimethylpolysiloxanes having high polymerization degrees and gummy dimethylsiloxane-methylphenylsiloxane copolymers having high polymerization degrees; and cyclosiloxane solutions of silicone rubber, trimethylsiloxysilicate, cyclosiloxane solutions of trimethylsiloxysilicate, higher alkoxy-modified silicones such as stearoxysilicone, higher fatty acid-modified silicones, alkyl-modified silicones, amino-modified silicones, fluorine-modified silicones, and silicone resin solutions. Examples of fluorinated oils are fluoro polyether, perfluorodecalin and perfluorooctane.

The blending amount of these oils B) depends on the oil type, but 1-98 wt % of the whole cosmetic material is suitable.

C) water can be blended with the cosmetic material of this invention according to the purpose. The blending amount depends on the type of agent, but 1-95 wt % of the whole cosmetic material is suitable.

One, two or more of the compounds D) having an alcoholic hydroxyl group in the molecular structure can be blended with the cosmetic material of this invention according to the purpose.

The compound D) having an alcoholic hydroxyl group in its molecular structure is preferably a water-soluble monohydric alcohol and/or a water-soluble polyhydric alcohol.

Examples of compounds having an alcoholic hydroxyl group which can be added in this invention are lower alcohols such as ethanol and isopropanol, sugar alcohols such as sorbitol and maltose, sterols such as cholesterol, sitosterol, phytosterol and lanosterol, and polyhydric alcohols such as butylene glycol, propylene glycol and dibutylene glycol. The blending amount may be within the range of 0.1-98 wt % of the whole cosmetic material.

The cosmetic material of this invention may also contain one, two or more of E) the water-soluble or water-swelling polymers.

Examples are gum arabic, tragacanth, arabino galactan, (carob gum), guar gum, karaya gum, carrageenan, pectin, agar, quince seed (i.e., marmelo) starch (rice, corn, potato, wheat), alge colloid, tranto gum and locust bean gum; microbial polymers, such as xanthan gum, dextran, succinoglucan and pullulan; animal derived polymers, such as collagen, casein, albumin and gelatin; starch derived polymers, such as carboxymethyl starch and methylhydroxypropyl starch; cellulose polymers, such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethylcellulose, crystalline cellulose and powdery cellulose; alginic acid derived polymers, such as sodium alginate and propylene glycol ester of alginic acid; vinyl polymers, such as polyvinyl methyl ether and carboxyvinyl polymer; polyoxyethylene polymers; polyoxyethylene-polyoxypropylene copolymers; acrylic polymers, such as sodium polyacrylate, polyethylacrylate and polyacrylamide; other synthetic water-soluble polymers, such as polyethyleneimines and cationic polymers; and inorganic water-soluble polymers, such as bentonite, aluminum magnesium silicate, montmorillonite, beidellite, nontronite, saponite, hectorite and silicic acid anhydride. In these water-soluble polymers, film-forming agents, such as polyvinyl alcohol and polyvinyl pyrrolidine, are also included. The blending amount is within the range of 0.1-25 wt % of total cosmetic material.

One, two or more of the powders and/or colorants F) other than the aforesaid surface-treated powder cosmetic materials A) of this invention may be used according to the purpose.

It is preferred that at least part of F), the powder and/or colorant, is a crosslinked silicone fine powder with dimethyl silicone crosslinks, polymethylsilsesquioxane powder, hydrophobic silica or a complex fine powder wherein a spherical silicone rubber surface is coated with polymethylsilsesquioxane particles, and more preferred that at least part of this F) powder and/or colorant is a powder and/or colorant having a fluorine group.

As in the case of the powder used as the A) surface-treated powder, provided that it is a powder used for ordinary cosmetic materials, the powder may have any form (spherical, acicular, tabular), particle diameter (fume, fine particle, pigment) or particle structure (porous, non-porous). Examples are inorganic powders, organic powders, surfactant metal salt powders, colored pigments, pearl pigments, metal powder pigments and natural pigments.

Complex powders, or powders treated with general oils, silicone oils, fluorine compounds and surfactants, whereof specific examples have been given above, may also be used provided that they do not interfere with the effect of this invention, one, two or more being used as required. The blending amount is preferably 0.1-99 wt % of the total cosmetic material. In particular, the blending amount in the case of a solid powder cosmetic material is 80-99 wt % of the total cosmetic material.

One, two or more of the G) surfactants can also be used for the cosmetic material of this invention according to the purpose. Examples of such surfactants are anionic, cationic, nonionic and amphoteric, there being no particular limitation, and any surfactant may be used provided that it is used in ordinary cosmetic materials.

It is preferred that this G) surfactant is a straight chain or branched silicone having a polyoxyalkylene chain in the molecule, and it is more preferred that the HLB of this G) surfactant is 2-8.

Examples of a usable anionic surfactant include fatty acid soap, such as sodium stearate or triethanolamine palmitate; alkyl ether carboxylic acids and salts thereof; salts of condensates of amino acids with fatty acids; alkanesulfonates; alkenesulfonates; sulfonated fatty acid esters; sulfonated fatty acid amides; sulfonates of formaldehyde condensate type; salts of alkylsulfates; salts of higher secondary alcohol sulfates; salts of alkyl and aryl ether sulfates; salts of fatty acid ether sulfates, salts of fatty acid alkylolamide sulfates; ether sulfates, such as salts of Turkey red oil sulfate; alkyl phosphate salts; ether phosphate salts; alkyl allyl ether phosphate salts; amide phosphate salts; and N-acylamino acid type surfactants.

Examples of a usable cationic surfactant include amine salts, such as alkylamine salts, polyamines and aminoalcohol fatty acid derivatives, quaternary alkylammonium salts, quaternary arylammonium salts, pyridinium salts and imidazolium salts.

Examples of a usable nonionic surfactant include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ehter, polyoxyethylene phytosterol ether, polyoxyethylene cholestanol ether, polyoxyethylene cholesteryl ether, polyoxyalkylene-modified organopoly-siloxanes, organopolysiloxanes modified with both polyoxyalkylene and alkyl groups, alkanolamides, sugar ethers and sugar amides; and examples of a usable amphoteric surfactant include betaine, aminocarboxylate, imidazoline derivatives and amidoamines. The blending proportion thereof is preferably in the range of 1-20 wt %, but more preferably 0.2-10 wt %, of the total cosmetic material.

One, two or more types of the H) crosslinked organopolysiloxane can also be used in the cosmetic material of this invention. The crosslinked organopolysiloxanes suitable for the present cosmetic materials are those which cause swelling when they contain a silicone having low viscosity of from 0.65 to 10.0 mm$^2$/sec (25° C.) in an amount larger than their own weight. The crosslinking agent of this crosslinked organopolysiloxane preferably has two or more vinyl reactive sites in the molecule, and forms a crosslinked structure by reaction between hydrogen atoms directly bonded to silicon atoms. A crosslinked organopolysiloxane comprising at least one moeity selected from a group comprising polyoxyalkylene, alkyl, alkenyl, aryl and fluoroalkyl in the crosslinked molecule can also be used. The blending amount when a crosslinked organopolysiloxane is used, is preferably 0.1-50 wt % but more preferably 1-30 wt %, of the total amount of cosmetic material.

One, two or more of the I) silicone resins can also be used for the cosmetic material of this invention according to the purpose, This silicone resin is preferably an acrylic silicone resin comprising an acrylic/silicone graft or block copolymer other than the aforesaid acrylic/silicone-copolymer. An acrylic silicone resin comprising at least one moeity in the molecule selected from among pyrolidone, long chain alkyl, polyoxyalkylene, fluoroalkyl portion and anions such as carboxylic acid, can also be used.

Further, this silicone resin is preferably a silicone reticular compound represented by MQ, MDQ, MT, MDT or MDTQ as a constituent component, wherein M means a mono-functional unit which is able to form a silicone polymer and is of formula $R_3SiO_{1/2}$, wherein each R is an organic moiety; D means a di-functional unit which is able to form a silicone polymer and is of formula $R_2SiO$, wherein each R is an organic moiety; T means a tri-functional unit which is able to form a silicone polymer and is of formula $RSiO_{3/2}$, wherein R is an organic moiety; and Q means a quad-functional unit which is able to form a silicone polymer and is of formula $SiO_2$. A silicone reticular compound containing at least one moeity in the molecule selected from among pyrrolidone, long chain alkyl, polyoxyalkylene, fluoroalkyl and amino can also be used.

The blending amount in the case of using a silicone resin such as an acrylic silicone resin or a silicone reticular compound, is preferably 0.1-20 wt %, but more preferably 1-10 wt %, relative to the total amount of cosmetic material.

To the present cosmetic material, the ingredients used in general cosmetic materials, such as water, a film-forming agent, an oil-soluble gelling agent, clay minerals modified with organic compounds, resins, ultraviolet absorbents, a moisture retention agent, antiseptics, an antimicrobial agent, perfume, salts, antioxidants, pH regulators, a chelating agent, refreshing agents, an anti-inflammatory agent, skin beautifying components (a skin whitener, a cell activator, a rough dry skin improver, a blood circulation promoter, a skin astringent and an anti-seborrheic agent), vitamins, amino acids, nucleic acids, hormones, clathrate compounds and hair fixing agents, can be added so far as they have no adverse influence on the effects of the present invention.

Examples of an oil-soluble gelling agent which can be added include metal soaps, such as aluminum stearate, magnesium stearate and zinc myristate; amino acid derivatives, such as N-lauroyl-L-glutamic acid and α,γ-di-n-butylamine; dextrin fatty acid esters, such as dextrin palmitic acid ester, dextrin stearic acid ester and dextrin 2-ethylhexaminic acid palmitic acid ester; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay. Examples of an antiperspirant which can be added may be selected from among aluminum chlorohydrate, aluminum chloride, aluminum sesquichlorohydrate, zirconyl hydroxychloride, aluminum zirconium hydroxychloride and aluminum zirconium glycine complex.

Examples of an ultraviolet absorbent which can be added include ultraviolet absorbents of benzoic acid type, such as p-aminobenzoic acid; those of anthranilic acid type, such as methyl anthranilate; those of salicylic acid type, such as methyl salicylate; those of succinic acid type, such as octyl p-methoxysuccinate; those of benzophenone type, such as 2,4-dihydroxybenzophenone; those of urocanic acid type, such as ethyl urocanate; and those of dibenzoylmethane type, such as 4-t-butyl-4'-methoxydibenzoylmethane. Examples of an ultraviolet absorption and scattering agent which can be added are powders which absorb and scatter ultraviolet light such as fine particle titanium oxide, fine particle iron-containing titanium oxide, fine particle zinc oxide, fine particle cerium oxide and their complexes.

Examples of a moisture retention agent which can be added include glycerin, sorbitol, propylene glycol, dipropylene glycol, 1,3-butylene glycol, glucose, xylitol, maltitol, polyethylene glycol, hyaluronic acid, chondroitin sulfuric acid, pyrrolidone carboxylic acid, polyoxyethylene glycoside, and polyoxypropylene methylglycoside.

Examples of an antiseptic agent which can be added include alkyl p-oxybenzoates, benzoic acid, sodium benzoate, sorbic acid, potassium sorbate and phenoxyethanol; and those of an antimicrobial agent which can be added include benzoic acid, salicylic acid, carbolic acid, sorbic acid, alkyl p-oxybenzoates, p-chlorometacresol, hexachlorophene, benzalkonium chloride, chlorohexydine chloride, trichlorocarbanilide, photosensitizer and phenoxyethanol.

Examples of an antioxidant which can be added include tocopherol, butylhydroxyanisole, dibutylhydroxytoluene and phytic acid; those of a pH regulator which can be added include lactic acid, citric acid, glycolic acid, succinic acid, tartaric acid, dl-malic acid, potassium carbonate, sodium hydrogen carbonate and ammonium hydrogen carbonate; those of a chelating agent which can be added include alanine, sodium ethylenediaminetetraacetate, sodium polyphosphate, sodium metaphosphate and phosphoric acid; those of a refrigerant which can be added include L-menthol and camphor; and those of an anti-inflammatory agent which can added include allantoin, glycyrrhizin and salts thereof, glycyrrhetinic acid and stearyl glycyrrhetinate, tranexamic acid and azulene.

Examples of a skin-beautifying component which can be added include whitening agents, such as placenta extract, arbutin, glutathione and Yukinoshita extract; cell activators, such as royal jelly, photosensitizer, cholesterol derivatives and calf blood extract; rough dry skin improvers; blood circulation improvers, such as nonylic acid vanillyl amide, benzyl nicotinate, β-butoxyethyl nicotinate, capsaicin, zingerone, cantharis tincture, ichtammol, caffeine, tannic acid, α-borneol, tocopheryl nicotinate, inositol hexanicotinate, cyclandelate, cinnarizine, tolazoline, acetyl choline, verapamil, cepharanthin and γ-oryzanol; skin astringents, such as zinc oxide and tannic acid; and anti-seborrheic agents, such as sulfur and thianthol.

Examples of vitamins which can be added include vitamin A, such as vitamin A oil, retinol, retinyl acetate and retinyl palmitate; vitamin B, including vitamin B2 such as riboflavin, riboflavin butyrate and flavin adenine nucleotide, vitamin B6 such as pyridoxine hydrochloride, pyridoxine dioctanoate and pyridoxine tripalmitate, vitamin B12 and its derivatives, and vitamin B15 and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as α-tocopherol, β-tocopherol, γ-tocopherol, dl-α-tocopheryl acetate, dl-α-tocopheryl nicotinate and dl-α-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of an amino acid which can be added include glycine, valine, leucine, isoleucine, serine, threonine, phenylaranine, alginine, lysine, aspartic acid, glutamic acid, cystine, cysteine, methionine, and tryptophan; those of a nucleic acid which can be added include deoxyribonucleic acid; and those of hormone which can be added include estradiol and ethenyl estradiol.

Examples of a hair fixing polymer compound are amphoteric, anionic, cationic or nonionic polymer compounds, e.g., polyvinyl pyrrolidone-polymer compounds such as polyvinyl pyrrolidone and vinyl pyrrolidone/vinyl acetate copolymer, acidic vinyl ether polymer compounds such as methyl vinyl ether/maleic anhydride alkyl half ester copolymer, acidic polyvinyl acetate-polymers such as vinyl acetate/crotonic acid copolymer, acidic acrylic polymer compounds such as (meth)acrylic acid/alkyl(meth)acrylate copolymer and (meth)acrylic acid/alkyl(meth)acrylate/alkyl acrylamide copolymer, and amphoteric acrylic-polymer compounds such as N-methacryloylethyl-N,N-dimethyl ammonium-alpha-N-methyl carboxy betaine/alkyl(meth)acrylate copolymer, hydroxypropyl(meth)acrylate/butylaminoethyl-methacrylate/ac rylic acid octylamide copolymer. Also, naturally-occurring polymer compounds such as cellulose or its derivatives, keratin, and collagen or its derivatives, can also be used.

The term "cosmetic material" as used herein is intended to include skin care products, such as face lotion, milky lotion, cream, face cleansing cream, packs, oily liquid, massage material, rinsing agent, deodorants, hand cream and lip cream; makeup products such as foundation, powder, liquid foundation, oily foundation, rouge, eye shadow, mascara, eyeliner, eyebrow makeup and lipstick; and hairdressing products, such as shampoo, rinse, treatment and sets; antiperspirant, and ultraviolet defense cosmetic materials such as suncut milky lotion or suncut cream.

Additionally, the present cosmetic material may have any form, including liquid, emulsion, cream, solid, paste, gel, powder, compress, layers, mousse, spray, stick or pencil.

EXAMPLES

This invention will now be described in more detail referring to specific examples, but this invention is not limited thereto. Unless otherwise specified, "%" refers to "wt %".

Manufacturing Example 1

100 wt parts of the radical polymerizing organopolysiloxane represented by the following formula (6), 10 wt parts of methyl methacrylate, 80 wt parts of stearyl methacrylate, 10 wt parts of γ-methacryloxypropyltrimethoxysilane, 200 wt parts of toluene and 4 wt parts of azobisisobutyronitrile were introduced into a glass flask provided with a stirrer, thermometer and reflux condenser, and heated in a nitrogen gas stream at 100° C. for 10 hours to carry out a polymerization reaction. Next, the toluene was distilled off under reduced pressure to obtain an acrylic fiber/silicone graft copolymer. This copolymer was a light yellow solid having a melting point of 30° C. The weight average molecular weight expressed as polystyrene by GPC was 42,000.

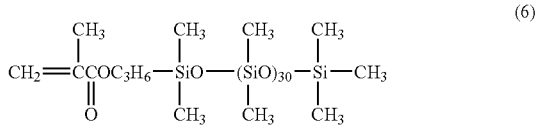

(6)

Manufacturing Example 2

In an identical way to that of Manufacturing Example 1, a copolymerization reaction was carried out with 100 wt parts of the radical polymerizing organopolysiloxane represented by formula (6), 60 wt parts of methyl methacrylate, 15 wt parts of butyl methacrylate, 15 wt parts of 2-ethylhexyl acrylate and 10 parts of γ-methacryloxy propyltriethoxysilane, to obtain an acrylic/silicone graft copolymer.

This copolymer was a light yellow, transparent resin having a melting point of 93° C. The weight average molecular weight expressed as polystyrene by GPC was 55,000.

Manufacturing Example 3

In an identical way to that of Manufacturing Example 1, a copolymerization reaction was carried out with 180 wt parts of the radical polymerizing organopolysiloxane represented by formula (7), 10 wt parts of methyl methacrylate and 10 wt parts of γ-methacryloxy propyltriethoxysilane, to obtain an acrylic/silicone graft copolymer.

This copolymer was a colorless, transparent liquid having a viscosity of 270 mm$^2$/sec at 25° C., specific gravity of 0.981 and refractive index of 1.4152. The weight average molecular weight expressed as polystyrene by GPC was 11,000.

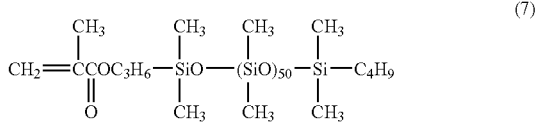

(7)

Examples 1-4 and Comparative Examples 1-4

Surface-treated powders were manufactured according to the following Table 1 using the acrylic/silicone graft copolymer obtained in Manufacturing Examples 1-2, and commercial processing agents.

TABLE 1

| Surface-treated powder | Powder | | Treatment Agent | | | |
| | Titanium oxide | Sericite | Manufacturing Example 1 | Manufacturing Example 2 | KF99 | KF9901 |
|---|---|---|---|---|---|---|
| Example 1 | 98 | | 2 | | | |
| Example 2 | 98 | | | 2 | | |
| Example 3 | | 95 | 5 | | | |
| Example 4 | | 95 | | 5 | | |
| Comp. Ex. 1 | 98 | | | | 2 | |
| Comp. Ex. 2 | 98 | | | | | 2 |
| Comp. Ex. 3 | | 95 | | | 5 | |
| Comp. Ex. 4 | | 95 | | | | 5 |

KF99: Methyl hydrogen polysiloxane, Shin-Etsu Chemical Industries
KF9901: Dimethyl methylhydrogen polysiloxane, Shin-Etsu Chemical Industries Manufacture of Surface-Treated Powder with Above Processing Agents;

98 parts (95 parts sericite) of untreated titanium oxide which had previously been dried under reduced pressure was introduced into a reactor, and a solution containing 2 parts (5 parts) of the above treatment agent diluted with toluene was gradually added with stirring. The temperature was raised to distil off toluene, and the product baked at 150° C. for 3 hours to manufacture the surface-treated powders of Examples 1-4 and Comparative Examples 1-4.

Next, the properties of the surface-treated powder obtained were measured regarding surface activity, water resistance and hydrogen generation amount. The results are shown in Table 2.

TABLE 2

| Surface-treated powder | Surface activity (δE) | Water resistance (hr) | Hydrogen generation amount (cc/g) |
|---|---|---|---|
| Example 1 | 2.0 | 6.0 | 0 |
| Example 2 | 1.0 | 5.5 | 0 |
| Example 3 | 2.5 | 5.5 | 0 |
| Example 4 | 1.0 | 5.0 | 0 |
| Comp. Ex. 1 | 2.0 | 3.5 | 2.2 |
| Comp. Ex. 2 | 4.0 | 4.5 | 3.5 |
| Comp. Ex. 3 | 1.0 | 6.0 | 3.5 |
| Comp. Ex. 4 | 3.0 | 4.5 | 4.0 |

Evaluation Method

Surface activity: 40 parts of the treated powder were kneaded with 60 parts of castor oil, a fixed amount was placed between glass slides, irradiated for a fixed time with ultraviolet light, and the color difference (δE) before and after irradiation was measured.

Water resistance: A fixed amount of the treated powder was pressed by an aluminum plate (50 mmΦ), a 1:1 mixture of 1,3-butylene glycol:water was dripped onto the powder to form water drops, and the absorption time was measured.

Hydrogen generation amount: To measure the remaining amount of Si—H radicals, a fixed amount of the powder was dispersed in toluene, a 20% KOH alkaline solution was dripped in, the hydrogen was collected, and its volume was measured.

The color change (color difference) increases, the higher is the surface activity of the powder. As can be seen from Table 2, in the surface-treated powders obtained from the acrylic/silicone graft copolymer of this invention, in Examples 1-4, no hydrogen at all is generated, surface activity is suppressed, and water resistance was excellent.

Examples 5-6 and Comparative Examples 5-6

Foundations were prepared having the compositions shown in the following Table 3 using the surface-treated powder obtained in Examples 1-4 and Comparative Examples 1-4, and evaluated.

TABLE 3

| | | Proportion (parts) | | | |
| Ingredient | | Ex. 5 | Ex. 6 | Comp.Ex. 5 | Comp.Ex. 6 |
|---|---|---|---|---|---|
| 1 | Titanium oxide of Example 1 | 12 | — | — | — |
| 2 | Sericite of Example 3 | 35 | — | — | — |

TABLE 3-continued

| Ingredient | Proportion (parts) | | | |
|---|---|---|---|---|
| | Ex. 5 | Ex. 6 | Comp.Ex. 5 | Comp.Ex. 6 |
| 3 Titanium oxide of Example 2 | — | 12 | — | — |
| 4 Sericite of Example 4 | — | 35 | — | — |
| 5 Titanium oxide of Comp.Ex. 1 | — | — | 12 | — |
| 6 Sericite of Comp.Ex. 3 | — | — | 35 | — |
| 7 Titanium oxide of Comp.Ex. 2 | — | — | — | 12 |
| 8 Sericite of Comp.Ex. 4 | — | — | — | 35 |
| 9 Lecithin-treated talc | 35.1 | 35.1 | 35.1 | 35.1 |
| 10 Lecithin-treated spheroidal nylon powder | 5 | 5 | 5 | 5 |
| 11 Red ochre | 0.4 | 0.4 | 0.4 | 0.4 |
| 12 Yellow iron oxide | 2 | 2 | 2 | 2 |
| 13 Amber | 0.4 | 0.4 | 0.4 | 0.4 |
| 14 Black iron oxide | 0.1 | 0.1 | 0.1 | 0.1 |
| 15 Dimethylpolysiloxane (6 mm$^2$/sec (25° C.)) | 7 | 7 | 7 | 7 |
| 16 Triioctanoic acid glyceryl | 1.5 | 1.5 | 1.5 | 1.5 |
| 17 Dipentaerithryte fatty acid ester | 1.5 | 1.5 | 1.5 | 1.5 |

(Manufacturing Process)
A: Ingredients 1-14 were mixed, and uniformly crushed.
B: Ingredients 15-17 were added to A, and crushed.
C: B was press-molded to manufacture a powder foundation.

The foundation obtained was tested by an expert panel of 50 women, and ease of use, light spreadablity, absence of smears and cosmetic lasting properties were evaluated according to the following criteria.

| Rating | Ease of use/cosmetic lasting properties | Lightness of spread | Absence of smearing |
|---|---|---|---|
| 5 | Good | Light | Good |
| 4 | Fairly good | Fairly light | Fairly good |
| 3 | Average | Average | Average |
| 4 | Rather poor | Rather heavy | Rather poor |
| 1 | Poor | Heavy | Poor |

The average points obtained were evaluated judged according to the following criteria.

Average point evaluation:
Average point obtained is 4.5 or higher: ⊚
Average point obtained is 3.5 to 4.5: ○
Average point obtained is 2.5 to 3.5: Δ
Average point obtained is 1.5 to 2.5: x
Average point obtained is less than 1.5; xx The results are shown in Table 4.

TABLE 4

| | Example 5 | Example 6 | Comp. Ex. 5 | Comp. Ex. 6 |
|---|---|---|---|---|
| Ease of use | ○ | ○ | Δ | ○ |
| Lightness of spread | ⊚ | ⊚ | ○ | ○ |
| Absence of smearing | ⊚ | ⊚ | ○ | ○ |
| Cosmetic lasting properties | ⊚ | ⊚ | ○ | X |

As seen from Table 4, the foundations of Examples 5 and 6 not only had lighter spreadability and were easier to use than those of Comparative Examples 5 and 6, but they left no smears and had good cosmetic lasting properties.

Moreover, when Comparative Example 5 which used a powder (Comparative Examples 1 and 3) treated by KF99 (methylhydrogen polysiloxane) was stored sealtight in state B of the aforesaid manufacturing methods, the container was observed to swell due to a dehydrogenation reaction of unreacted Si—H groups.

Method of Manufacturing Various Surface-Treated Powders, and Examples of Various Cosmetic Preparations Using these Powders 98 parts of the powders which had been previously heat-treated by drying under reduced pressure were introduced into a reactor, and a solution comprising 2 parts of one of the aforesaid acrylic/silicone graft copolymers (Manufacturing Examples 1-3) diluted by toluene was gradually added with stirring. The temperature was raised to distil off toluene, and the product was baked at 150° C. for 3 hours with stirring. The surface-treated powder obtained was returned to room temperature in a current of nitrogen, and used for various cosmetic preparations.

Example 7

Oil-in-Water Type Cream

| (Ingredients) | Weight (%) |
|---|---|
| 1. Ethanol | 17.0 |
| 2. Propylene glycol | 3.0 |
| 3. Polyether-modified silicone (NB 1) | 0.5 |
| 4. Glyceryl tri-isooctanoate | 2.0 |
| 5. Acrylic/ silicone graft copolymer (Manufacturing Example 1)-treated sericite | 3.0 |
| 6. Hybrid silicone composite powder (NB 2) | 5.0 |
| 7. Carboxyvinyl polymer (1% solution) | 20.0 |
| 8. Xanthan gum (2% solution) | 6.0 |
| 9. Triethanolamine | 0.2 |
| 10. Preservative | Suitable amount |
| 11. Perfume | Suitable amount |
| 12. Purified water | 60.8 |

(NB 1) Shin-Etsu Chemical Industries Ltd.: KF-6011 (brand name)
(NB 2) Shin-Etsu Chemical Industries Ltd.: KSP-100 (brand name)

(Manufacturing Method)
A: Ingredients 1-6 were mixed.
B: Ingredients 7-12 were mixed and dissolved.
C: A was added to B, and stirred to form an emulsion.

The oil-in-water cream obtained as described above had a fine texture, spread lightly, was not tacky or oily, was fresh and moist, and left a clean feel. The cosmetic preparation lasted very well, showed no change with temperature or time, and had excellent stability.

Example 8

Oil-in-Water Type Cream

| | (Ingredient) | Weight (%) |
|---|---|---|
| 1. | Crosslinked dimethylpolysiloxane (NB 1) | 10.0 |
| 2. | Glyceryl trioctanoate | 5.0 |
| 3. | Dipropylene glycol | 7.0 |
| 4. | Glycerin | 5.0 |
| 5. | Methylcellulose (2% solution) (NB 2) | 7.0 |
| 6. | Polyacrylamide emulsifying agent (NB 3) | 2.0 |
| 7. | Acrylic/silicone graft copolymer (Manufacturing Example 2)- treated mica titanium | 1.0 |
| 8. | Preservative | Suitable amount |
| 9. | Perfume | Suitable amount |
| 10. | Purified water | 63.0 |

(NB 1) Crosslinked dimethylpolysiloxane: KSG-16 (Shin-Etsu Chemical Industries Ltd.)
(NB 2) Methyl cellulose; Metrose SM-4000 (Shin-Etsu Chemical Industries Ltd.)
(NB 3): Polyacrylamide emulsifying agent: Sepigel 305 (SEPIC)

(Manufacturing Method)
A: Ingredients 3-10 were mixed.
B: Ingredients 1-2 were mixed, dissolved, and added to A with stirring to form an emulsion.

The oil-in-water type cream obtained as described above had a fine texture, spread lightly, was not tacky or oily, was fresh and moist, and left a clean feel. The cosmetic preparation lasted very well, showed no change with temperature or time, and had excellent stability.

Example 9

Water-in-Oil Type Cream

| | (Ingredient) | Weight (%) |
|---|---|---|
| 1. | Dimethylpolysiloxane (6 mm$^2$/sec (25° C.)) | 6.0 |
| 2. | Methylphenyl polysiloxane | 4.0 |
| 3. | Squalane | 5.0 |
| 4. | Dioctanoic acid neopentyl glycol | 3.0 |
| 5. | Polyether-modified silicone (NB 1) | 3.0 |
| 6. | Hydrophobic particle titanium oxide (NB 2) | 2.0 |
| 7. | Magnesium sulfate | 0.7 |
| 8. | Glycerin | 10.0 |
| 9. | Preservative | Suitable amount |
| 10. | Perfume | Suitable amount |
| 11. | Purified water | Remainder |

(NB 1) Polyether-modified silicone: KF6012 (Shin-Etsu Chemical Industries Ltd.)
(NB 2) Hydrophobically-treated titanium oxide particles: Particulate titanium oxide having an average particle diameter of 0.05 μm was dispersed in water to 10 wt %, and sodium silicate solution (SiO$_2$/Na$_2$O mole ratio = 0.5) was added corresponding to 2 wt % relative to titanium oxide in terms of SiO$_2$, and thoroughly stirred.Next, 10 wt % aluminium sulfate solution corresponding to 7.5 wt % titanium oxide in terms of Al$_2$O$_3$ was gradually added, and hydrated silicic acid and hydrated alumina were deposited on the surface of the titanium oxide.After the reaction was complete, the product was filtered, washed and dried, and crushed by a jet mill.The product was transferred to a Henschel mixer, 2 wt % of the acrylic/silicone graft copolymer (Manufacturing Example 3) was added while stirring thoroughly, mixed and stirred, and baked at 120° C.

(Manufacturing Process)
A: Ingredients 1-5 were mixed with heating, ingredient 6 was added, and the mixture blended uniformly.
B: Ingredients 7-9 and 11 were dissolved with heating.
C: B was gradually added to A with stirring to form an emulsion, cooled, and ingredient 10 was added to obtain a cream.

The water-in-oil type cream obtained as described above had a fine texture, spread lightly, was not tacky or oily, was fresh and moist, and left a clean feel. The cosmetic preparation lasted very well, showed no change with temperature or time, and had excellent stability.

Example 10

Water-in-Oil Type Cream

| | (Ingredient) | Weight (%) |
|---|---|---|
| 1. | Alkyl-modified crosslinked polyether-modified silicone (NB 1) | 6.0 |
| 2. | Liquid paraffin | 13.5 |
| 3. | Macadamia nut oil | 5.0 |
| 4. | Alkyl/polyether co-modified silicone (NB 2) | 0.5 |
| 5. | Hybrid silicone compound powder (NB 3) | 3.0 |
| 6. | Acrylic/silicone graft copolymer (Manufacturing Example 2)- treated particulate titanium oxide | 2.0 |
| 7. | Sodium citrate | 0.2 |
| 8. | Propylene glycol | 8.0 |
| 9. | Glycerin | 3.0 |
| 10. | Preservative | Suitable amount |
| 11. | Perfume | Suitable amount |
| 12. | Purified water | 58.8 |

(NB 1) Alkyl-modified crosslinked polyether-modified silicone: KSG-31 (Shin-Etsu Chemical Industries Ltd.)
(NB 2) Alkyl/polyether co-modified silicone: KF-6026 (Shin-Etsu Chemical Industries Ltd.)
(NB 3) Hybrid silicone composite powder: KSP-100 (Shin-Etsu Chemical Industries Ltd.)

(Manufacturing Process)
A: Ingredients 1-6 were mixed.
B: Ingredients 7-12 were mixed and dissolved, and A was added with stirring to form an emulsion.

The cream obtained as described above had a fine texture, spread lightly, was not tacky or oily, was fresh and moist, and left a clean feel. The cosmetic preparation lasted very well, showed no change with temperature or time, and had excellent stability.

Example 11

Water-in-Oil Type Cream

| | (Ingredient) | Weight (%) |
|---|---|---|
| 1. | Decamethylcyclopentasiloxane | 16.0 |
| 2. | Dimethylpolysiloxane (6 mm$^2$/sec (25° C.)) | 4.0 |
| 3. | Polyether-modified silicone (NB 1) | 5.0 |
| 4. | POE(5) octyldodecyl ether | 1.0 |
| 5. | Mono-polyoxyethylene stearate sorbitan (20 E.O.) | 0.5 |
| 6. | Anhydrous silicic acid-treated zinc oxide (NB 2) | 2.0 |
| 7. | Acrylic/silicone graft copolymer (Manufacturing Example 2)-treated particulate titanium oxide | 10.0 |
| 8. | Liquid paraffin | 2.0 |
| 9. | Macadamia nut oil | 1.0 |
| 10. | Scutellaria root extract (NB 3) | 1.0 |
| 11. | Gentiana extract (NB 4) | 0.5 |
| 12. | Ethanol | 5.0 |
| 13. | 1,3-butylene glycol | 2.0 |
| 14. | Preservative | Suitable amount |
| 15. | Perfume | Suitable amount |
| 16. | Purified water | Remainder |

(NB 1) Polyether-modified silicone: KF6017 (Shin-Etsu Chemical Industries Ltd.)
(NB 2) Anhydrous silicic acid-treated zinc oxide: Silica of particle diameter 0.01–10 μm containing 50% occluded zinc oxide; Sansfair SZ-5 (Asahi Glass Ltd.)
(NB 3) Scutellaria root: exttracted with 50% 1,3 butylene glycol water
(NB 4) Gentiana extract: extracted with 20% ethanol water (Manufacturing Process)
A: Components 6-9 were uniformly mixed and dispersed.
B: Ingredients 1-5 were mixed, and A was added.
C: Ingredients 10-14 and 16 were mixed, then B was added to form an emulsion.
D: C was cooled, and adding ingredient 15 was added to obtain a cream.

The water-in-oil type cream thus obtained had a fine texture, was not tacky, spread lightly, had good skin contact, good setting properties and sheen. The cosmetic preparation lasted very well, showed no change with temperature or time, and had excellent stability.

Example 12

Eyeliner

| | (Ingredient) | Weight (%) |
|---|---|---|
| 1. | Decamethylcyclopentasiloxane | 39.0 |
| 2. | Polyether-modified silicone (NB 1) | 3.0 |
| 3. | Organosilicon resin (NB 2) | 15.0 |
| 4. | Dioctadecyldimethylammonium salt-modified montmorillonite | 3.0 |
| 5. | Acrylic/silicone graft copolymer (Manufacturing Example 1)-treated black iron oxide | 10.0 |
| 6. | 1,3-butylene glycol | 5.0 |
| 7. | Sodium dehydroacetate | Suitable amount |

| | (Ingredient) | Weight (%) |
|---|---|---|
| 8. | Preservative | Suitable amount |
| 9. | Purified water | Remainder |

(NB 1) Polyether-modified silicone: KF-6017 (Shin-Etsu Chemical Industries)
(NB 2) Organosilicon resin: KF-7312J (Shin-Etsu Chemical Industries)

(Manufacturing Process)
A: Ingredients 1-4 were mixed, and Ingredient 5 was added.
B: Ingredients 6-9 were mixed.
C: B was gradually added to A to form an emulsion, and an eyeliner was thereby obtained.

The eyeliner obtained as described above spread lightly, was easy to draw with, had a cool, clean feel and was not tacky. It showed no change with temperature or time, was very easy to use with excellent stability, and not only had superior water and sweat resistance, but also a long-lasting effect.

Example 13

Foundation

| | (Ingredient) | Weight (%) |
|---|---|---|
| 1. | Decamethylcyclopentasiloxane | 45.0 |
| 2. | Dimethyl polysiloxane (6 mm$^2$/sec (25° C.)) | 5.0 |
| 3. | Polyether-modified silicone (NB 1) | 2.0 |
| 4. | Octadecyl dimethylbenzyl ammonium salt-modified montmorillonite | 4.0 |
| 5. | Acrylic/silicone graft copolymer (Manufacturing Example 1)-treated titanium oxide | 10.0 |
| 6. | Acrylic/silicone graft copolymer (Manufacturing Example 1)-treated talc | 6.0 |
| 7. | Acrylic/silicone graft copolymer (Manufacturing Example 1)-treated mica | 6.0 |
| 8. | Acrylic/silicone graft copolymer (Manufacturing Example 1)-treated red ochre | 1.6 |
| 9. | Acrylic/silicone graft copolymer (Manufacturing Example 1)-treated yellow iron oxide | 0.7 |
| 10. | Acrylic/silicone graft copolymer (Manufacturing Example 1)-treated black iron oxide | 0.2 |
| 11. | Dipropylene glycol | 5.0 |
| 12. | Paraoxybenzoic acid methyl ester | 0.3 |
| 13. | 2-amino-2-methyl-1,3-propanediol | 0.2 |
| 14. | Hydrochloric acid | 0.1 |
| 15. | Perfume | Suitable amount |
| 16. | Purified water | Remainder |

(NB 1) Polyether-modified silicone: KF-6017 (Shin-Etsu Chemical Industries)

(Manufacturing Process)
A: Ingredients 1-5 were mixed with heating, and ingredients 6-11 were added to make a uniform mixture.
B: Ingredients 12-14 and 16 were dissolved with heating (pH of the aqueous system is 9.0).
C: A and B were gradually added with stirring, the mixture was cooled, and ingredient 15 was added to obtain a foundation.

The foundation obtained as mentioned above had a fine texture, spread lightly without tackiness or oiliness, was moist and fresh, and left a clean feel. The cosmetic preparation lasted very well, showed no change with temperature or time, and had excellent stability.

Example 14

Eye Shadow

| (Ingredients) | Weight (%) |
|---|---|
| 1. Decamethylcyclopentasiloxane | 15.0 |
| 2. Dimethylpolysiloxane (6 mm$^2$/sec (25° C.)) | 10.0 |
| 3. Polyether-modified branched silicone (NB 1) | 2.0 |
| 4. PEG (10) lauryl ether | 0.5 |
| 5. Acrylic/silicone graft copolymer (Manufacturing Example 2)-treated chromium oxide | 6.2 |
| 6. Acrylic/silicone graft copolymer (Manufacturing Example 2)-treated ultramarine blue | 4.0 |
| 7. Acrylic/silicone graft copolymer (Manufacturing Example 2)-treated titanium coated mica | 6.0 |
| 8. Sodium chloride | 2.0 |
| 9. Propylene glycol | 8.0 |
| 10. Preservative | Suitable amount |
| 11. Perfume | Suitable amount |
| 12. Purified water | Remainder |

(NB 1) Polyether-modified branched silicone: KF6028 (Shin-Etsu Chemical Industries Ltd.)

(Manufacturing Process)
A: Ingredients 1-4 were mixed, Ingredients 5-7 were added, and uniformly dispersed.
B: Ingredients 8-10 and 12 were uniformly dissolved.
C: B was gradually added to A with stirring to form an emulsion, and Ingredient 11 was added to obtain an eye shadow.

The eye shadow obtained as mentioned above spread lightly without oiliness or powderiness, was moist and fresh, and left a clean feel. It had good water resistance, water repellance and sweat resistance. The cosmetic preparation did not easily disintegrate, showed no change with temperature or time, and had excellent stability.

Example 15

Lipstick

| (Ingredient) | Weight (%) |
|---|---|
| 1. Candellila wax | 8.0 |
| 2. Polyethylene wax | 8.0 |
| 3. Long-chain alkyl-containing acrylic silicone resin (NB 1) | 12.0 |
| 4. Methylphenylpolysiloxane (NB 2) | 3.0 |
| 5. Isononanic acid isotridecyl | 20.0 |
| 6. Isostearic acid glyceryl | 16.0 |
| 7. Triisostearic acid polyglycyl | 28.5 |
| 8. Acrylic/silicone graft copolymer (Manufacturing Example 3)-treated red 202 | 0.8 |
| 9. Acrylic/silicone graft copolymer (Manufacturing Example 3)-treated red ochre | 1.5 |
| 10. Acrylic/silicone graft copolymer (Manufacturing Example 3)-treated yellow iron oxide | 1.0 |
| 11. Acrylic/silicone graft copolymer (Manufacturing Example 3)-treated black iron oxide | 0.2 |
| 12. Acrylic/silicone graft copolymer (Manufacturing Example 3)-treated titanium oxide | 1.0 |
| 13. Preservative | Suitable amount |
| 14. Perfume | Suitable amount |

(NB 1) Long-chain alkyl-containing acrylic/silicone resin: KP-561 (Shin-Etsu Chemical Industries Ltd.)
(NB 2) Methylphenyl polysiloxane: KF-54 (Shin-Etsu Chemical Industries Ltd.)

(Manufacturing Process)
A: Ingredients 1-6 and part of 7 were mixed with heated, and dissolved.
B: Ingredients 8-14 and the remainder of 7 were uniformly mixed, added to A and rendered homogeneous.

The lipstick obtained as mentioned above spread lightly without oiliness or powderiness, and left a clean feel. It had good water resistance and water repellance, lasted well and had excellent stability.

Example 16

Eyeliner

| (Ingredient) | Weight (%) |
|---|---|
| 1. Decamethylcyclopentasiloxane | 6.0 |
| 2. Dimethylpolysiloxane (6 mm$^2$/sec (25° C.)) | 5.0 |
| 3. Jojoba oil | 2.0 |
| 4. Polyether-modified silicone (NB 1) | 1.0 |
| 5. Alkyl/polyether co-modified silicone (NB 2) | 1.0 |
| 6. Acrylic silicone resin (NB 3) | 15.0 |
| 7. Acrylic/silicone graft copolymer (Manufacturing Example 3)-treated black iron oxide | 20.0 |
| 8. Ethanol | 5.0 |
| 9. Preservative | Suitable amount |
| 10. Purified water | Remainder |

(NB 1) Polyether-modified silicone: KF6017 (Shin-Etsu Chemical Industries Ltd.)
(NB 2) Alkyl/polyether co-modified silicone: KF6026 (Shin-Etsu Chemical Industries Ltd.)
(NB 3) Acrylic silicone resin: KP545 (Shin-Etsu Chemical Industries)

(Manufacturing Process)
A: Ingredients 1-4 were mixed with heating, and Ingredient 5 was added and uniformly dispersed.
B: Ingredients 6-8 were dissolved with heating.
C: B was gradually added to A with stirring to make an emulsion, and an eyeliner was thus obtained.

The eyeliner obtained as mentioned above spread lightly without oiliness or powderiness, was moist and fresh, and left a clean feel.

It had good water resistance, water repellance and sweat resistance. The cosmetic preparation did not easily disintegrate, showed no change with temperature or time, and had excellent stability.

Example 17

Liquid Emulsion Foundation

| (Ingredient) | Weight (%) |
|---|---|
| 1. Dimethylpolysiloxane (6 mm$^2$/sec (25° C.)) | 4.5 |
| 2. Decamethylcyclopentasiloxane | 15.0 |
| 3. Squalane | 4.0 |
| 4. Dioctanoic acid neopentyl glycol | 3.0 |
| 5. Myristic acid isostearic acid diglyceride | 2.0 |
| 6. α-Monoisostearyl glyceryl ether | 1.0 |
| 7. Polyether-modified silicons (NB 1) | 1.0 |
| 8. Alkyl/polyether co-modified silicone (NB 2) | 0.5 |
| 9. Aluminum distearate | 0.2 |
| 10. Acrylic/silicone graft copolymer (Manufacturing Example 2)-treated titanium oxide | 5.0 |
| 11. Acrylic/silicone graft copolymer (Manufacturing Example 2)-treated sericite | 2.0 |
| 12. Acrylic/silicone graft copolymer (Manufacturing Example 2)-treated talc | 3.0 |
| 13. Acrylic/silicone graft copolymer (Manufacturing Example 2)-treated red ochre | 0.4 |
| 14. Acrylic/silicone graft copolymer (Manufacturing Example 2)-treated yellow iron oxide | 0.7 |
| 15. Acrylic/silicone graft copolymer (Manufacturing Example 2)-treated black iron oxide | 0.1 |
| 16. Magnesium sulfate | 0.7 |
| 17. Glycerin | 3.0 |
| 18. Preservative | Suitable amount |
| 19. Perfume | Suitable amount |
| 20. Purified water | Remainder |

(NB 1) Polyether-modified silicone: KF6017 (Shin-Etsu Chemical Industries Ltd.)
(NB 2) Alkyl/polyether co-modified siliicone: KF6026 (Shin-Etsu Chemical Industries Ltd.)

(Manufacturing Process)

A: Ingredients 1-9 were mixed with heating, and Ingredients 10-15 were added to make a uniform mixture.

B: Ingredients 16-18 and 20 were dissolved with heating.

C: B was gradually added to A with stirring, cooled, and Ingredient 19 was added to obtain a liquid emulsification foundation.

The liquid emulsification foundation described above had a low viscosity, had a fine texture, spread lightly without tackiness or oiliness, was moist and fresh, and left a clean feel. The cosmetic preparation lasted very well, showed no change with temperature or time, and had excellent stability.

Example 18

Liquid Foundation

| (Ingredient) | Weight (%) |
|---|---|
| 1. Decamethylcyclopentasiloxane | 16.0 |
| 2. Dimethylpolysiloxane (6 mm$^2$/sec (25° C.)) | 8.0 |
| 3. Paramethoxycinnamic acid octyl | 3.0 |
| 4. 12-hydroxystearic acid | 1.0 |
| 5. Fluorine-modified silicone (NB 1) | 15.0 |
| 6. Fluoroalkyl/polyether co-modified silicone (NB 2) | 5.0 |
| 7. Spheroidal polymethylsilsesquioxane powder (NB 3) | 3.0 |
| 8. Acrylic/silicone graft copolymer (Manufacturing Example 1)-treated particulate titanium oxide | 8.0 |
| 9. Acrylic/silicone graft copolymer (Manufacturing Example 1)-treated mica titanium | 1.0 |
| 10. Acrylic/silicone graft copolymer (Manufacturing Example 1)-treated titanium oxide | 5.0 |
| 11. Acrylic/silicone graft copolymer (Manufacturing Example 1)-treated red ochre | 0.9 |
| 12. Acrylic/silicone graft copolymer (Manufacturing Example 1) yellow iron oxide | 2.0 |
| 13. Acrylic/silicone graft copolymer (Manufacturing Example 1)-treated black iron oxide | 1.0 |
| 14. Ethanol | 15.0 |
| 15. Glycerin | 3.0 |
| 16. Magnesium sulfate | 1.0 |
| 17. Preservative | Suitable amount |
| 18. Perfume | Suitable amount |
| 19. Purified water | Remainder |

(NB 1) Fluorine-modified silicone: FL-50 (Shin-Etsu Chemical Industries Ltd.)
(NB 2) Fluoroalkyl/polyether co-modified silicone: FPD-4694 (Shin-Etsu Chemical Industries Ltd.)
(NB 3) Spheroidal polymethylsilsesquioxane powder: KMP590 (Shin-Etsu Chemical Industries Ltd.)

(Manufacturing Process)

A: Ingredients 7-13 were uniformly mixed.

B: Ingredients 1-6 were mixed with heating to 70° C., A was added, and uniformly mixed and dispersed.

C: Ingredients 14-17 and 19 were heated to 40° C., B was gradually added to form an emulsion, cooled, and Ingredient 18 was added to obtain a liquid foundation.

The liquid foundation obtained as described above was not tacky, spread liightly, and had a clean, very cool feel. The cosmetic preparation showed no change with temperature or time, and had excellent stability.

Example 19

Eyeliner

| (Ingredient) | Weight (%) |
|---|---|
| 1. Decamethylcyclopentasiloxane | 22.0 |
| 2. Dimethylpolysiloxane (6 mm$^2$/sec (25° C.) | 5.0 |
| 3. Acrylic/silicone graft copolymer (Manufacturing Example 1)-treated black iron oxide | 20.0 |
| 4. Organosilicon resin (NB 1) | 10.0 |
| 5. Vitamin E acetate | 0.2 |
| 6. Jojoba oil | 2.0 |
| 7. Bentonite | 3.0 |
| 8. Polyether-modified silicone (NB 2) | 2.0 |
| 9. Ethanol | 3.0 |
| 10. 1,3-butylene glycol | 5.0 |

| (Ingredient) | Weight (%) |
| --- | --- |
| 11. Preservative | Suitable amount |
| 12. Purified water | Remainder |

(NB 1) Organosilicon resin: KF-7312J (Shin-Etsu Chemical Industries Ltd.)
(NB 2) Polyether-modified silicone: KF6017 (Shin-Etsu Chemical Industries Ltd.)

(Manufacturing Process)

A: Ingredients 1-2 and 4-7 were mixed, Ingredient 3 was added, and uniformly mixed and dispersed.

B: Ingredients 8-10 and 12 were mixed.

C: B was gradually added to A to make an emulsion, cooled, and Ingredient 11 was added to obtain an eyeliner.

The eyeliner obtained as mentioned above spread lightly, was easy to draw with, and had a cool, clean feel without tackiness. It showed no change with temperature or time, was easy to use, and had excellent stability.

It also had excellent water resistance and sweat resistance, and was found to last very well.

Example 20

Foundation

| (Ingredient) | Weight (%) |
| --- | --- |
| 1. Decamethylcyclopentasiloxane | 27.0 |
| 2. Methylphenyl polysiloxane | 3.0 |
| 3. Trioctanic acid glyceryl | 10.0 |
| 4. Polyether-modified silicone (NB 1) | 1.0 |
| 5. Mono-isostearic acid polyglyceryl | 3.0 |
| 6. Hydrophobically-treated mixed powder (NB 2) | 18.0 |
| 7. Red ochre | 1.2 |
| 8. Yellow iron oxide | 2.6 |
| 9. Black iron oxide | 0.2 |
| 10. 1,3-butylene glycol | 7.0 |
| 11. Sodium chloride | 0.5 |
| 12. Preservative | Suitable amount |
| 13. Perfume | Suitable amount |
| 14. Ppurified water | Remainder |

(NB 1) Polyether-modified silicone: KF6017 (Shin-Etsu Chemical Industries Ltd.)
(NB 2) Hydrophobically-treated mixed powder
| | | |
| --- | --- | --- |
| a. | Fine particulate titanium oxide | 8.0 |
| b. | Fine particulate zinc oxide | 4.0 |
| c. | Talc | 3.0 |
| d. | Mica | 3.0 |

(Manufacturing Process)

A: Ingredients a-d were mixed, 1 wt % of acrylic/silicone graft copolymer (Manufacturing Example 1) was added to these powders, and heat treatment was applied.

B: Ingredients 1-5 were mixed, dissolved with heating, and Ingredients 6-9 were uniformly dispersed.

C: Ingredients 10-12 and 14 were mixed, and B was added to make an emulsion.

D: C was cooled, and Ingredient 13 was added to obtain a foundation.

The foundation obtained as described above was not tacky, spread lightly, had good skin contact, good setting properties and sheen.

The cosmetic preparation lasted very well, showed no change with temperature or time, and had excellent stability.

Example 21

Brushing Agent Spray

| (Ingredient) | Weight (%) |
| --- | --- |
| 1. Myristic acid isopropyl | 1.0 |
| 2. Stearyl trimethylammonium chloride | 0.05 |
| 3. Acrylic/silicone graft copolymer (Manufacturing Example 1)-treated particulate zinc oxide | 3.0 |
| 4. Ethanol | 25.0 |
| 5. Perfume | Suitable amount |
| 6. Propellant | Remainder |

(Manufacturing Process)

A: Ingredients 1-5 were mixed.

B: An aerosol can was filled with A, and Ingredient 6 added to obtain a brushing agent.

The brushing agent spray obtained as described above had a good sheen, was very smooth and had excellent durability. The dispersibility of the powder was excellent, combing was easy, and a very good result with sheen was obtained.

Example 22

Rinse

| (Ingredient) | Weight (%) |
| --- | --- |
| 1. Distearic acid ethylene glycol | 3.0 |
| 2. Cetanol | 2.0 |
| 3. Mono-stearic acid propylene glycol | 3.0 |
| 4. Dimethylpolysiloxane (100 mm$^2$/sec (25° C.)) | 3.0 |
| 5. Mono-stearic acid glycerin | 4.0 |
| 6. Polyoxyethylene (3) stearate | 4.0 |
| 7. Acetyl chloride trimethylammonium | 5.0 |
| 8. Polyoxyethylene (20) cetyl ether | 2.0 |
| 9. Acrylic/silicone graft copolymer (Manufacturing Example 1)-treated zinc oxide | 2.0 |
| 10. 1,3-butylene glycol | 5.0 |
| 11. Preservative | Suitable amount |
| 12. Perfume | Suitable amount |
| 13. Purified water | Remainder |

(Manufacturing Process)

A: Ingredients 1-9 were stirred, and mixed.

B: Ingredients 10-11 and 13 were mixed with heating.

C: B was added to A and mixed, cooled, and Ingredient 12 was added to obtain a rinse.

The rinse obtained as described above was neither tacky nor heavy in use, gave an excellent sheen to the hair, and left the hair soft, smooth and full. The preparation was very easy to use while combing the hair, and was highly durable.

Example 23

Rinse-in Shampoo

| (Ingredients) | Weight (%) |
|---|---|
| 1. Lauric acid amidopropyldimethylaminoacetic acid betaine (30%) | 15.0 |
| 2. Polyoxyethylene (3) lauryl ether sodium sulfate (27%) | 4.0 |
| 3. Polyoxyethylene (150) distearate | 0.5 |
| 4. Cationic cellulose (4%) | 0.5 |
| 5. Glycerin | 3.0 |
| 6. Dimethyl polysiloxane (1,000,000 mm$^2$/sec (25° C.)) | 1.0 |
| 7. Dimethyl polysiloxane (100 mm$^2$/sec (25° C.)) | 3.0 |
| 8. Acrylic/silicone graft copolymer (Manufacturing Example 1)-treated mica | 2.0 |
| 9. Preservative | Suitable amount |
| 10. Perfume | Suitable amount |
| 11. Purified water | Remainder |

(Manufacturing Process)
A: Ingredients 1-5, 9 and 11 were heated and mixed.
B: Ingredients 6-8 were mixed, and dispersed.
C: B was added to and mixed with A, cooled, and Ingredient 10 was added to obtain a rinse-in shampoo. The rinse-in shampoo obtained as described above was neither tacky nor heavy in use, gave an excellent sheen to the hair, and left the hair soft, smooth and full. The preparation was very easy to use while combing the hair, and was highly durable.

Example 24

Treatment

| (Ingredient) | Weight (%) |
|---|---|
| 1. Distearic acid ethylene glycol | 1.0 |
| 2. Liquid paraffin | 10.0 |
| 3. Squalane | 5.0 |
| 4. Stearyl alcohol | 1.5 |
| 5. Dimethyl polysiloxane (10 mm$^2$/sec (25° C.)) | 3.0 |
| 6. Stearic acid | 6.0 |
| 7. Polyoxyethylene (3) stearyl alcohol | 4.5 |
| 8. Polyoxyethylene (150) cetyl ether | 2.0 |
| 9. Acrylic/silicone graft copolymer (Manufacturing Example 3) - treated sericite | 1.5 |
| 10. 1,3-butylene glycol | 6.0 |
| 11. Preservative | Suitable amount |
| 12. Perfume | Suitable amount |
| 13. Purified water | Remainder |

(Manufacturing Process)
A: Ingredients 1-9 were heated, and mixed.
B: Ingredients 10-11 and 13 were mixed, and dispersed.
C: B was added to and mixed with A, cooled, and Ingredient 12 was added to obtain a treatment.

The treatment obtained as described above was neither tacky nor heavy in use, gave an excellent sheen to the hair, and left the hair soft, smooth and full. The preparation was very easy to use while combing the hair, and was highly durable.

Example 25

Water-in-Oil Type Antiperspirant

| (Ingredient) | Weight (%) |
|---|---|
| 1. Crosslinked polyether-modified silicone (NB 1) | 7.0 |
| 2. Decamethylcyclopentasiloxane | 10.0 |
| 3. Trioctanic acid glyceryl | 7.0 |
| 4. Dipropylene glycol | 5.0 |
| 5. Sodium citrate | 0.2 |
| 6. Aluminum/zirconium tetrachlorohydrate | 18.0 |
| 7. Acrylic/silicone graft copolymer (Manufacturing Example 2) - treated zinc oxide | 5.0 |
| 8. Fluorine-modified hybrid silicone composite powder (NB 2) | 2.0 |
| 9. Perfume | Suitable amount |
| 10. Purified water | 45.8 |

(NB 1) Crosslinked polyether-modified silicone: KSG-21 (Shin-Etsu Chemical Industries Ltd.)
(NB 2) Fluorine-modified hybrid silicone composite powder: KSP-200 (Shin-Etsu Chemical Industries Ltd.)

(Manufacturing Process)
A: Ingredients 1-3 were mixed.
B: Ingredients 4-10 were mixed.
C: B was added to A, mixed and emulsified.

The water-in-oil antiperspirant obtained as described above spread lightly, had a cool, clean feel and was not tacky or oily. It showed no change with temperature or time, was very easy to use and very stable.

Example 26

Roll-On Antiperspirant

| (Ingredient) | Weight (%) |
|---|---|
| 1. Crosslinked polyether-modified silicone (NB 1) | 20.0 |
| 2. Dimethylpolysiloxane (6 mm$^2$/sec (25° C.)) | 10.0 |
| 3. Crosslinked dimethylpolysiloxane (NB 2) | 15.0 |
| 4. Decamethyl cyclopentasiloxane | 30.0 |
| 5. Aluminum/zirconium tetrachlorohydrate | 20.0 |
| 6. Acrylic/silicone graft copolymer (Manufacturing Example 1) - treated zinc oxide | 5.0 |
| 7. Perfume | Suitable amount |

(NB 1) Crosslinked polyether-modified silicone: KSG-21 (Shin-Etsu Chemical Industries Ltd.)
(NB 2) Crosslinked dimethyl polysiloxane: KSG-15 (Shin-Etsu Chemical Industries Ltd.)

(Manufacturing Process)
A: Ingredients 1-4 were mixed.
B: Ingredients 5-7 were added to A, and uniformly dispersed.

The roll-on antiperspirant obtained as described above spread lightly, had a cool, clean feel and was not tacky or oily. It showed no change with temperature or time, was very easy to use and very stable.

Example 27

Sunscreen Milky Lotion

| (Ingredients) | Weight (%) |
|---|---|
| 1. Decamethylcyclopentasiloxane | 20.0 |
| 2. Methylphenylpolysiloxane | 3.0 |
| 3. Mono-isostearic acid sorbitan | 1.0 |
| 4. Polyether-modified silicone (NB 1) | 0.5 |
| 5. Trimethylsiloxysilicic acid (NB 2) | 1.0 |
| 6. Paramethoxycinnamic acid octyl | 4.0 |
| 7. Acrylic/silicone graft copolymer (Manufacturing Example 1) - treated particulate titanium oxide | 8.0 |
| 8. Sorbitol | 2.0 |
| 9. Sodium chloride | 2.0 |
| 10. Preservative | Suitable amount |
| 11. Perfume | Suitable amount |
| 12. Purified water | Remainder |

(NB 1) Polyether-modified silicone: KF6015 (Shin-Etsu Chemical Industries Ltd.)
(NB 2) Trimethylsiloxysilicic acid: X-21-5250 (Shin-Etsu Chemical Industries Ltd.)

(Manufacturing Process)
A: Ingredients 1-6 were mixed with heating, and Ingredient 7 was uniformly dispersed.
B: Ingredients 8-10 and 12 were mixed with heating.
C: B was added to A with stirring to form an emulsion, cooled, and Ingredient 11 was added to obtain a sunscreen milky lotion.

The sunscreen milky lotion obtained as described above had a fine texture, spread lightly, was not tacky, and was fresh and moist. Also, as the cosmetic preparation lasted well, its ultraviolet radiation blocking effect was maintained, it showed no change with temperature or time, and had excellent stability.

Example 28

Suncut Cream

| (Ingredient) | Weight (%) |
|---|---|
| 1. Decamethylcyclopentasiloxane | 17.5 |
| 2. Acrylic silicone resin (NB 1) | 12.0 |
| 3. Tri isooctanoic acid glyceryl | 5.0 |
| 4. Paramethoxycinnamic acid octyl | 6.0 |
| 5. Crosslinked polyether-modified silicone (NB 2) | 5.0 |
| 6. Alkyl/polyether co-modified silicone (NB 3) | 1.0 |
| 7. Acrylic/silicone graft copolymer (Manufacturing Example 2) - treated zinc oxide | 20.0 |
| 8. Sodium chloride | 0.5 |
| 9. 1,3-butylene glycol | 2.0 |
| 10. Preservative | Suitable amount |
| 11. Perfume | Suitable amount |
| 12. Purified water | Remainder |

(NB 1) Acrylic silicone resin: KP545 (Shin-Etsu Chemical Industries Ltd.)
(NB 2) Crosslinked polyether-modified silicone: KSG21 (Shin-Etsu Chemical Industries Ltd.)
(NB 3) Alkyl/polyether co-modified silicone: KF6026 (Shin-Etsu Chemical Industries Ltd.)

(Manufacturing Process)
A: Ingredient 2 was added to part of Ingredient 1 and mixed uniformly, Ingredient 7 was added, and dispersed by a bead mill.
B: The remainder of Ingredient 1 and Ingredients 3-6 were mixed, and blended uniformly.
C: Ingredients 8-10 and 12 were mixed, and dissolved.
D: C was added to B to make an emulsion, then A and Ingredient 11 were added to obtain a suncut cream.

The suncut cream obtained as described above was not tacky, spread lightly, had good skin contact, good setting properties and left the skin silky. The cosmetic preparation lasted very well, showed no change with temperature or time, and had excellent stability.

INDUSTRIAL USE

The surface-treated powder of this invention treated with the acrylic/silicone graft copolymer compound has blocked surface activity, and excellent water resistance. Therefore, cosmetic preparations which use the surface-treated powder of this invention spread lightly, are not oily, are fresh and moist and leave a clean feel. They also have very good dispersibility, sebum resistance and cosmetic lasting properties. Moreover, they show no change with temperature or time, and have excellent stability, which demonstrates the significance of this invention.

What is claimed is:

1. A surface-treated powder which is obtained by treating a surface of said powder with an acrylic/silicone copolymer having at least one hydrolyzable silyl group in its molecule so that said copolymer is adsorbed on the surface of the powder, then dried and sintered,
   wherein the powder is at least one selected from the group consisting of inorganic powders, organic powders, surfactant metal salt powders, colored pigments, pearl pigments, metal powder pigments and natural pigments; and the proportion of the acrylic/silicone copolymer relative to 100 wt parts of the powder before surface treatment is 0.1-30 wt parts;
   wherein the acrylic/silicone copolymer is obtained by copolymerization of 1-97 wt % of an organopolysilixane compound of formula (1):

$$A-\underset{R^1}{\overset{R^1}{\underset{|}{\overset{|}{SiO}}}}-(\underset{R^1}{\overset{R^1}{\underset{|}{\overset{|}{SiO}}}})_n-\underset{R^1}{\overset{R^1}{\underset{|}{\overset{|}{Si}}}}-R^1 \quad (1)$$

wherein,
A is a radical polymerizing group of formula (4) or (5):

$$CH_2=C(R^2)COOR^3- \quad (4)$$

$$CH_2=C(R^2)C_6H_5- \quad (5)$$

wherein
$R^2$ is hydrogen or methyl,
$R^3$ is an alkylene group having 1-10 carbon atoms, and n is 3-500,
$R^1$ are organic groups selected from alkyl groups, aryl, aralkyl and fluorine-substituted alkyl groups having 1-30 carbon atoms, which are identical or different; and 2-95 wt % of the acrylic monomer of formula (2):

$$CH_2=C(R^4)COOR^5 \quad (2)$$

wherein,
R⁴ is hydrogen or methyl, and
R⁵ is an alkyl group having 1-30 carbon atoms; and
1-10 wt % of the radical polymerizing silane compound of formula (3):

B—Si(CH₃)₃₋ₘ(OR⁶)ₘ    (3)

wherein,
B is a radical polymerizing of formula (6) or (7):

CH₂=C(R⁷)COOR⁸—    (6)

CH₂=C(R⁷)C₆H₅—    (7)

wherein,
R⁷ is hydrogen or methyl,
R⁸ is an alkylene group having 1-10 carbon atoms,
R⁶ is an alkyl group or alkenyl group having 1-4 carbon atoms, and
m is 1-3.

2. The surface-treated powder according to any of claim 1, wherein said powder is zinc oxide, titanium oxide or an extender pigment.

3. A cosmetic material comprising the A) surface-treated powder described in any of claim 1.

4. The cosmetic material according to claim 3, further comprising at least one of
B) an oil,
C) water,
D) a compound having an alcoholic hydroxyl group in its molecular structure,
E) a water-soluble or water-swelling polymer,
F) a powder and/or colorant which is not the surface-treated powder A),
G) a surfactant,
H) a crosslinked organopolysiloxane, and
I) a silicone resin.

5. The cosmetic material according to claim 4, wherein at least part of said B) oil is a liquid at ordinary temperature.

6. The cosmetic material according to claim 4, wherein at least part of said B) oil is a straight chain or cyclic silicone oil represented by R⁹ₐSiO₍₄₋ₐ₎/₂
wherein
R⁹ is hydrogen or an organic group, which is an alkyl group, aryl group, aralkyl group or fluorine-substituted alkyl group having 1-30 carbon atoms, and
0<=a<=2.5.

7. The cosmetic material according to any of claim 4, wherein at least part of said B) oil is an oil having a fluorine group or an amino group.

8. The cosmetic material according to claim 4, wherein D) the compound having an alcoholic hydroxyl group in its molecular structure is a water-soluble, monohydric alcohol and/or a water-soluble polyhydric alcohol.

9. The cosmetic material according to claim 4, wherein at least part of F) the powder and/or colorant is a crosslinked silicone fine powder having a crosslinked dimethylsilicone structure, a hydrophobic silica, or a composite powder wherein a spheroidal silicone rubber surface is coated with polymethyl silsesquioxane particles.

10. The cosmetic material according to claim 4, wherein at least part of F) the powder and/or colorant is a powder and/or colorant comprising fluorine groups.

11. The cosmetic material according to claim 4, wherein G) the surfactant is a straight chain or branched silicone having a polyoxyalkylene chain in the molecule.

12. The cosmetic material according to claim 4, wherein the HLB of G) the surfactant is 2-8.

13. The cosmetic material according to claim 4, wherein H) the crosslinked organopolysiloxane is a crosslinked organopolysiloxane containing at least its own weight of a silicone having a low viscosity of 0.65 mm²/sec (25° C.)-10.0 mm²/sec (25° C.).

14. The cosmetic material according to claim 4, wherein H) the crosslinked organopolysiloxane is a crosslinked organopolysiloxane comprising two or more vinylic and reactive sites in the molecule, and is formed by reaction with a hydrogen atom directly bonded to a silicon atom.

15. The cosmetic material according to any of claim 14, wherein H) the crosslinked organopolysiloxane is a crosslinked organopolysiloxane comprising at least one part polyoxyalkylene, alkyl, aryl and fluoroalkyl moiety in its crosslinked molecule.

16. The cosmetic material according to claim 4, wherein I) the silicone resin is an acrylic/silicone resin other than the acrylic/silicone copolymer.

17. The cosmetic material according to claim 4, wherein I) the silicone resin is an acrylic/silicone resin comprising at least one pyrrolidone, long chain alkyl, polyoxyalkylene, fluoroalkyl or carboxylic acid moiety.

18. The cosmetic material according to claim 4, wherein I) the silicone resin is a reticular silicone compound comprising at least one pyrrolidone, long chain alkyl, polyoxyalkylene, fluoroalkyl or amino moiety.

19. The cosmetic material according to any of claim 3, wherein the form of the product is a liquid, emulsion, cream, solid, paste, gel, powder, compress, laminate, mousse, spray, stick or pencil.

20. A skin care cosmetic material, comprising a skin care cosmetic material carrier and the cosmetic material according to claim 3.

21. A makeup cosmetic material, comprising a makeup cosmetic material carrier and the cosmetic material according to claim 3.

22. A hair care cosmetic material, comprising a hair care cosmetic material carrier and the cosmetic material according to claim 3.

23. An antiperspirant cosmetic material, comprising an antiperspirant cosmetic material carrier and the cosmetic material according to claim 3.

24. An ultraviolet defense cosmetic material, comprising an ultraviolet defense cosmetic material carrier and the cosmetic material according to claim 3.

25. The skin care cosmetic material according to claim 20, wherein the form of the product is a liquid, emulsion, cream, solid, paste, gel, powder, compress, laminate, mousse, spray, stick or pencil.

26. The makeup cosmetic material according to claim 21, wherein the form of the product is a liquid, emulsion, cream, solid, paste, gel, powder, compress, laminate, mousse, spray, stick or pencil.

27. The hair care cosmetic material according to claim 22, wherein the form of the product is a liquid, emulsion, cream, solid, paste, gel, powder, compress, laminate, mousse, spray, stick or pencil.

28. The antiperspirant cosmetic material according to claim 23, wherein the form of the product is a liquid, emulsion, cream, solid, paste, gel, powder, compress, laminate, mousse, spray, stick or pencil.

29. The ultraviolet defense cosmetic material according to claim 24, wherein the form of the product is a liquid, emulsion, cream, solid, paste, gel, powder, compress, laminate, mousse, spray, stick or pencil.

30. The surface-treated powder according to claim 1, wherein the acrylic/silicone copolymer is obtained by copolymerization of 5-90 wt % of an organopolysiloxane compound of formula (1), 2-60 wt % of an acrylic monomer of formula (2), and 2-7 wt % of a radical polymerizing silane compound of formula (3).

31. The surface-treated powder according to claim 1, wherein the molecular weight of the acrylic/silicone copolymer is 5,000-200,000 expressed as weight average molecular weight of polystyrene as measured by GPC.

32. The surface-treated powder for the cosmetic material according to claim 1, wherein 2-60 wt % of an acrylic monomer of formula (2) is used in the copolymerization.

33. The surface-treated powder for the cosmetic material according to claim 1, wherein the adsorption is performed by dispersing said powder in a treatment agent comprising the acrylic/silicone copolymer and water or organic solvent; or mixing the powder with the treatment agent and treating with ball mill or jet mill; then drying and sintering the product.

34. The surface-treated powder for the cosmetic material according to claim 1, wherein the adsorption is performed by dispersing said powder in a treatment agent comprising the acrylic/silicone copolymer and water or organic solvent; then drying and sintering the product.

35. The surface-treated powder for the cosmetic material according to claim 32, wherein the adsorption is performed by dispersing said powder in a treatment agent comprising the acrylic/silicone copolymer and water or organic solvent; or mixing the powder with the treatment agent and treating with ball mill or jet mill; then drying and sintering the product.

36. The surface-treated powder for the cosmetic material according to claim 32, wherein the adsorption is performed by dispersing said powder in a treatment agent comprising the acrylic/silicone copolymer and water or organic solvent; then drying and sintering the product.

* * * * *

UNITED STATES PATENT AND TRADEMARK OFFICE
CERTIFICATE OF CORRECTION

PATENT NO. : 7,722,899 B2
APPLICATION NO. : 10/479993
DATED : May 25, 2010
INVENTOR(S) : Ono et al.

It is certified that error appears in the above-identified patent and that said Letters Patent is hereby corrected as shown below:

Column 32, line 42 reads "copolymerization of 1-97 wt % of an organopolysilixane" should read -- copolymerization of 1-97 wt % of an organopolysilioxane --

Column 32, line 65 reads "2-95 wt % of the acrylic monomer of formula (2):" should read -- 2-95 wt % of an acrylic monomer of formula (2): --

Column 33, line 9 reads "B is a radical polymerizing of formula (6) or (7):" should read -- B is a radical polymerizing group of formula (6) or (7): --

Column 33, line 24, reads "powder described in any of claim 1." should read -- powder according to claim 1. --

Column 34, line 13 reads "crosslinked organopolysiloxane comprising at least one part" should read -- crosslinked organopolysiloxane comprising at least one --

Signed and Sealed this

Seventeenth Day of August, 2010

David J. Kappos
*Director of the United States Patent and Trademark Office*